United States Patent
Andronic

(10) Patent No.: US 8,219,025 B2
(45) Date of Patent: Jul. 10, 2012

(54) STAND ALONE SENSOR APPARATUS FOR CONTINUOUS WEB MACHINES

(75) Inventor: Cristian Andronic, Burnaby (CA)

(73) Assignee: Honeywell International Inc., Morristown, NJ (US)

( * ) Notice: Subject to any disclaimer, the term of this patent is extended or adjusted under 35 U.S.C. 154(b) by 1120 days.

(21) Appl. No.: 12/102,647

(22) Filed: Apr. 14, 2008

(65) Prior Publication Data

US 2009/0258604 A1     Oct. 15, 2009

(51) Int. Cl.
*H04B 5/00*     (2006.01)

(52) U.S. Cl. .......... 455/41.1; 455/73; 455/88; 455/131; 455/343.1; 340/12.5; 340/10.5; 340/10.34; 375/222; 375/316; 713/320

(58) Field of Classification Search .......... 455/41.1, 455/73, 131, 343.1, 343.2, 88; 375/222, 375/316; 713/320; 370/338
See application file for complete search history.

(56) References Cited

U.S. PATENT DOCUMENTS

| | | | |
|---|---|---|---|
| 6,813,542 B2 * | 11/2004 | Peshkin et al. | 700/245 |
| 6,907,317 B2 * | 6/2005 | Peshkin et al. | 700/245 |
| 7,120,508 B2 * | 10/2006 | Peshkin et al. | 700/87 |
| 7,148,499 B2 * | 12/2006 | Lapstun et al. | 250/566 |
| 7,235,890 B1 | 6/2007 | Jasinski | |
| 7,567,822 B2 * | 7/2009 | Hart et al. | 455/562.1 |
| 7,819,034 B2 * | 10/2010 | Jasinski | 73/866.5 |
| 7,872,574 B2 * | 1/2011 | Betts et al. | 340/539.26 |
| 7,949,433 B2 * | 5/2011 | Hern et al. | 700/284 |
| 2005/0192710 A1 * | 9/2005 | Thornton et al. | 700/284 |
| 2008/0129495 A1 * | 6/2008 | Hitt | 340/539.26 |

OTHER PUBLICATIONS

Tom Rosenberg, Product Line Manager, Balluff Inc., Understanding non-contact transmission of power and sensor signals', Design News, Jun. 1, 2001, www.designnews.com, 7 pages.

* cited by examiner

*Primary Examiner* — Marceau Milord

(57) ABSTRACT

A stand alone sensor apparatus includes a moveable chassis and, mounted to the chassis, a wireless power receiver, a sensor, and a wireless transceiver. The wireless power receiver receives power wirelessly, converts the wireless power to electrical power, and provides the electrical power to the sensor and the wireless transceiver. The sensor measures a characteristic of a continuous web material. The wireless transceiver is coupled to the sensor and wirelessly sends a signal that is based upon the measured characteristic. An air source and/or a temperature control device may be mounted to the moveable chassis and receive electrical power from the wireless power receiver.

20 Claims, 2 Drawing Sheets

STAND ALONE SENSOR APPARATUS FOR CONTINUOUS WEB MACHINES

TECHNICAL FIELD

This disclosure relates generally to control systems and more specifically to an apparatus, system and method for a standalone sensor for a continuous web application.

BACKGROUND

A continuous web (CW) machine processes a continuous sheet of material that is conveyed through the machine. Some CW machines manufacture the material, such as a paper manufacturing machine. Other CW machines process existing material, such as a pattern printing machine. Other machines may both manufacture and process, such as a rubber calendaring machine.

A CW machine typically includes one or more sensors for sensing characteristics of the material being manufactured or processed. For example, a paper manufacturing machine may include one or more sensors for color, surface gloss, basis weight, and/or other paper characteristics.

SUMMARY

This disclosure provides an apparatus, system and method for a standalone sensor for a continuous web application.

In one embodiment, an apparatus includes a moveable chassis and, mounted to the chassis, a wireless power receiver, a sensor, and a wireless transceiver. The wireless power receiver receives power wirelessly, converts the wireless power to electrical power, and provides the electrical power to the sensor and the wireless transceiver. The sensor measures a characteristic of a continuous web material. The wireless transceiver is coupled to the sensor and wirelessly sends a signal that is based upon the measured characteristic.

In another embodiment, a system includes a wireless power source, a track, a chassis moveably coupled to the track, and a supervisory controller. Mounted to the moveable chassis are a wireless power receiver, a sensor, and a wireless transceiver. The wireless power receiver receives power wirelessly from the wireless power source, converts the wireless power to electrical power, and provides the electrical power to the sensor and the wireless transceiver. The sensor measures a characteristic of a continuous web material. The wireless transmitter wirelessly sends a signal that is based upon the measured characteristic. The supervisory controller controls motion of the moveable chassis and wirelessly receives the signal.

In yet another embodiment, a method includes receiving power wirelessly from a wireless power source at a sensor moveably coupled to a track and converting the wireless power to electrical power. The method also includes measuring a characteristic of a continuous web material using the sensor, which operates with the electrical power. The method further includes wirelessly transmitting a signal that is based upon the measured characteristic using the electrical power.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
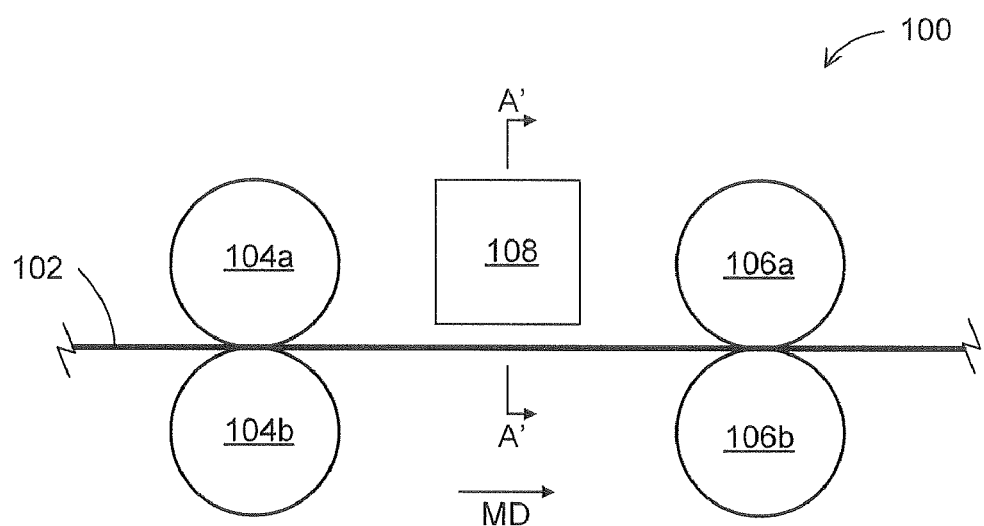
FIG. 1 presents a schematic side view of a sensor apparatus in a continuous web machine.

FIG. 1 presents a schematic side view of a sensor apparatus in a continuous web machine 100. A continuous web material 102 is transported through the machine 100 by means of roller pairs 104 and 106. The roller pair 104a and 104b pull the material 102 from previous stages of the machine 100. The roller pair 106a and 106b feed the material 102 into later stages of the machine 100. The material 102 moves in a direction referred to as the "machine direction" as indicated by an arrow MD in FIG. 1.

Between the roller pairs 104 and 106, a sensor apparatus 108 is positioned close to one side of the continuous web material 102. In some cases, the sensor 108 extends across the material 102, but more typically the sensor 108 moves across the width of the material 102, in a direction that is into and out of the page in FIG. 1.

Although FIG. 1 illustrates one example of a continuous web machine 100, various changes may be made to FIG. 1. For example, the sensor 108 could be located at any location in the machine 100 or on either or both sides of the material 102. The sensor may be located opposite a roller or drum, rather than in a space between rollers.

Figure 2:
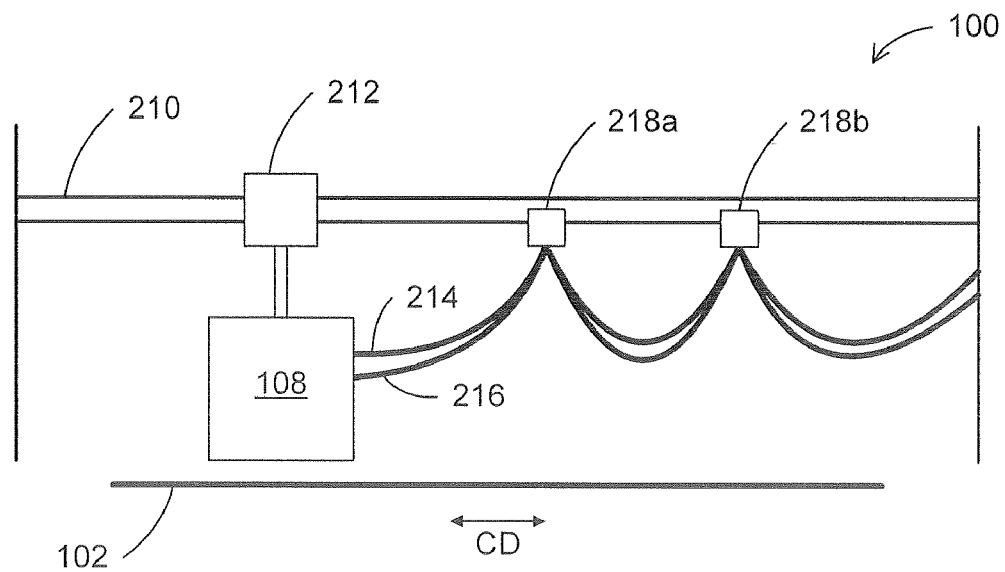
FIG. 2 presents a schematic front view of the sensor apparatus of FIG. 1.

FIG. 2 presents a schematic front view of the sensor apparatus of FIG. 1, generally in the plane A'-A' indicated in FIG. 1. The sensor apparatus 108 includes a carriage 212 that moveably mounts the sensor 108 to a track 210. A motorized mechanism moves the carriage 212 along the track to position the sensor 108 at a desired location above the continuous web material 102. The motorized mechanism may employ a belt or screw mechanism to move the sensor 108.

The sensor apparatus 108 receives supply inputs such as cooling fluid and/or compressed air and returns spent cooling fluid via one or more cables (or hoses) 214. The sensor apparatus 108 also send sensor measurement data to a process monitoring and/or control system via wired communication links in a cable, ribbon cable or other conductor 216. Carriages 218a and 218b support the cables 214 and 216 so as not to touch the material 102. The carriages 218 may be unpowered, or the motorized mechanism that moves the carriage 212 may also move the carriages 218a and 218b.

Figure 3:
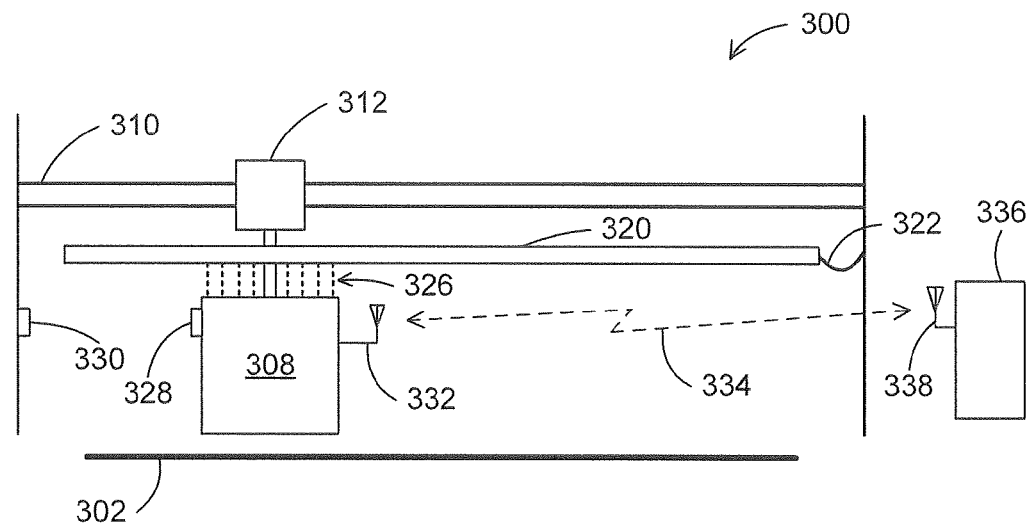
FIG. 3 presents a schematic front view of a stand alone sensor according to one embodiment of this disclosure in a continuous web machine.

FIG. 3 presents a schematic front view of a stand alone sensor 308 according to one embodiment of this disclosure in a continuous web machine 300. The sensor apparatus 308 includes a carriage 312 that moveably mounts the sensor 308 to a track 310. The sensor 308 is positioned close to one side of a continuous web material 302.

The sensor 308 receives power wirelessly from a wireless power transmitter 320, which receives power via a cable 322. In the embodiment of FIG. 3, the power transmitter 320 is inductively coupled to a wireless power receiver in the sensor apparatus 308 as indicated by broken lines 326. The power transmitted wirelessly is converted into electrical power and used to power devices in the sensor apparatus 308, as explained in greater detail with reference to FIG. 4. The power transmitter 320 may include a single large induction loop or a plurality of smaller loops. It will be understood that in other embodiments, other wireless power transmission techniques may be used.

The sensor apparatus 308 also includes a coupling device 328. When the sensor 308 is moved to one end of the track 310, the coupling device 328 mates with a fitting 330. Via the fitting 330 and the coupling device 328, storage tanks within the sensor apparatus 308 may be charged with compressed air or other supply materials needed to operate mechanisms and/or devices within the sensor apparatus 308.

The sensor apparatus 308 also includes an antenna 332 by which the sensor 308 can communicate wirelessly to a measurement subsystem (MSS) 336. The MSS 336 also includes an antenna 338. The MSS 336 is in wired or wireless communication with one or more of a process control system, a monitoring application, a process historian application, or other process control related applications.

The MSS may receive a read command from the process control system or monitor application and cause the sensor apparatus 308 to make one or more measurements of one or more characteristics of the continuous web material 302. Where the material 302 is paper, such characteristics may include color, surface gloss, and/or basis weight. The sensor apparatus 308 then wirelessly sends a signal 334 to the MSS 336 representing the measured characteristics. The MSS 336, in turn, reports the measured characteristics to the process control or monitoring application that issued the read command.

The process control system or monitor application may configure the MSS 336 to cause the sensor apparatus 308 to make measurements automatically and wirelessly signal them back to the MSS 336. The MSS 336 may send the measurement information when requested by monitor/control system. In other embodiments, the MSS 336 may 'push' measurements or alarms back to the monitor application when certain preconfigured criteria are met.

A motorized mechanism under the control of the MSS 336 moves the carriage 312 along the track to position the sensor 308 at a desired location above the continuous web material 302. The motorized mechanism may be coupled to the carriage 312 or to a chassis of the sensor apparatus 308 by a belt, a screw mechanism, or other mechanical linkage that enables the motorized mechanism to move the sensor 308 along the track 310.

In another embodiment, the wireless power transmitter 320 may be the active windings of a linear motor. Such a linear motor may be a linear induction motor or a linear synchronous motor. The windings may both impel the moveable chassis of the sensor apparatus 308 along the track 310, as well as wirelessly transmit power to the sensor 308.

Figure 4:
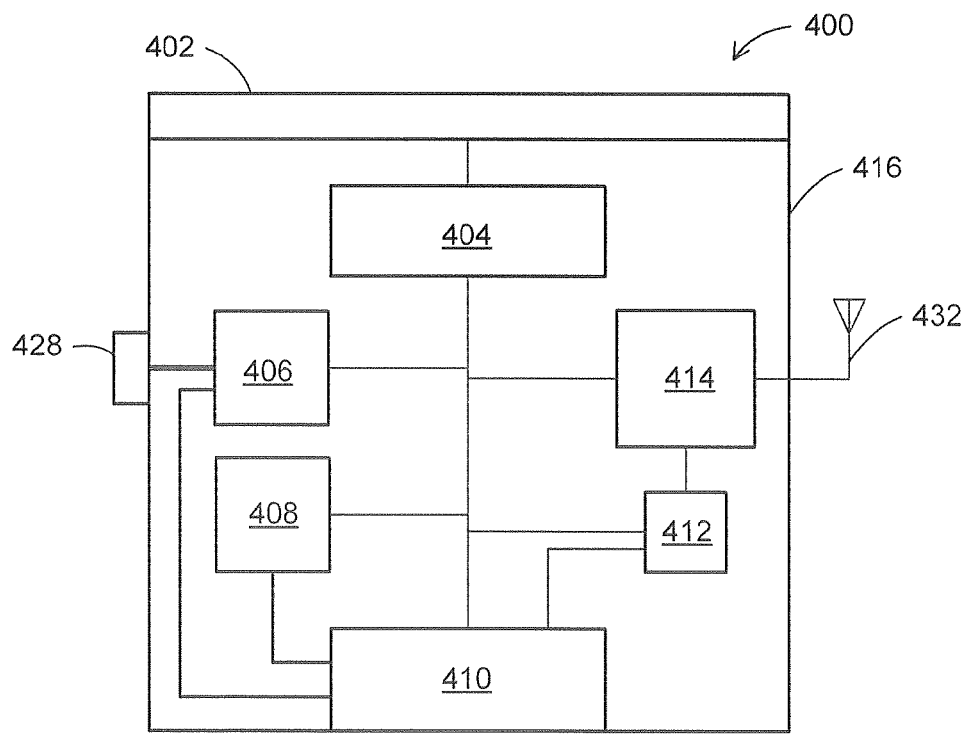
FIG. 4 illustrates a schematic view of a stand alone sensor according to one embodiment of this disclosure.

FIG. 4 illustrates a schematic view of a stand alone sensor apparatus 400 according to one embodiment of this disclosure. The sensor 400 includes a moveable chassis 416 to which is mounted a wireless power receiver 402 and a power convertor 404. Also mounted to the chassis 416 are a controller 412 and a wireless transceiver 414, which is coupled to an antenna 432. An air source 406, a coupling device 428, and a temperature control device 408 are also mounted to the chassis 416. Also mounted to the chassis is a sensor device 410.

The wireless power receiver 402 receives power from a wireless power transmitter and conducts the received power to the power convertor 404, which converts the received power to a form suitable for use by other devices in the sensor apparatus 400. The power convertor 404 may include a battery, capacitor, or other power storage device to provide power during periods when the power receiver 402 is not within range of a power transmitter or is positioned between adjacent power receivers.

The sensor device 410 is one or more sensors that measure a characteristic of the paper, foil, rubber, or other continuous web material moving past the sensor apparatus 400. The sensor device 410 receives electrical power from the power convertor 404. Often, the sensor device 410 is half of a two part sensor whose parts lie on opposite sides of the continuous web material. The sensor device 410 may include one or more sensors that measure the transmission of radiation through the material to measure basis weight, the reflection of infrared radiation by the material to measure water content, or the distance between calipers touching each side of the material to measure thickness.

The controller 412 receives power from the power convertor 404 and is coupled to, and controls operation of, the sensor device 410. The controller 412 receives signals from, and sends signals to, the wireless transmitter 414, which receives and transmits wireless signals 432 via the antenna 432. The controller 412 receives commands and configuration messages and, in response, configures and operates the sensor device 410. The controller 412 transmits information via the wireless transceiver 414 relating to sensor measurement results and status of the sensor apparatus 400.

Under the control of the controller 412, the temperature control device 408 maintains the sensor device 410 and the other devices in the sensor apparatus 400 at a temperature at which they operate properly and remain calibrated. Typically, the environment in which the sensor apparatus 400 operates is hot, and the temperature control device 408 is a chiller. A working fluid of the chiller 408, such as glycol, may circulate through a base plate of the sensor apparatus 400 to cool the sensor device 410. The heated working fluid may then pass through a radiator or other device to transfer heat from the base plate away from the sensor apparatus 400. The air within the moveable chassis 416 may be cooled by the working fluid, in order to reduce or prevent condensation on the devices of the sensor apparatus 400.

The air source 406 may be a compressed air tank or other source of high-pressure air. Such pressurized air may be used, under the control of the controller 412, to inflate bellows to extend a caliper to contact a surface of the continuous web material being measured. Compressed air may also be used to open a shutter to release beta or gamma radiation for a measurement of basis weight. Furthermore, compressed air may be used to blow away debris that can collect on a sensor window of the sensor device 410.

The compressed air tank may be supplied with air by an air compressor mounted to the moveable chassis 416. In other embodiments, the compressed air tank may be coupled to a coupling device 428. When the sensor apparatus 400 is moved to a docking position, the coupling device 428 mates with a fitting and receives compressed air to replenish the supply in the compressed air tank.

As used herein, the term "wireless" communication indicates the transmission of data via an ambient medium, for example, air. A non-wireless communication includes a communication achieved by transmission of data via a physical conduit, channel, or other communication path. Examples of such physical communication paths for non-wireless communication include copper or other conductive wires, optical fibers, coaxial and other cables, and any of a plethora of other known or to be developed communication or transmission lines. No specific structure is implied by either term (wireless or non-wireless), nor is the use of a particular band of frequencies, wavelengths, bit rates, or modulation protocols implied.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
a moveable chassis, the chassis adapted to be moveably coupled to a track and move back and forth across a surface of a continuous web material that is being manufactured or processed;
a wireless power receiver mounted to the moveable chassis and adapted to receive power wirelessly and convert the wireless power to electrical power;
a sensor mounted to the moveable chassis and adapted to receive electrical power from the wireless power receiver and to measure a characteristic of the continuous web material; and
a wireless transceiver mounted to the moveable chassis and adapted to inductively receive electrical power from the wireless power receiver and to wirelessly send a first signal that is based upon the measured characteristic.

2. The apparatus of claim 1, further comprising:
a controller mounted to the moveable chassis and adapted to receive a second signal based upon the measured characteristic and generate the first signal based upon the second signal.

3. The apparatus of claim 1, further comprising:
a power storage device adapted to receive electrical power from the wireless power receiver and to provide electrical power to the sensor and the wireless transceiver.

4. An apparatus comprising:
a moveable chassis;
a wireless power receiver mounted to the moveable chassis and adapted to receive power wirelessly and convert the wireless power to electrical power;
a sensor mounted to the moveable chassis and adapted to receive electrical power from the wireless power receiver and to measure a characteristic of a continuous web material;
a wireless transceiver mounted to the moveable chassis, the wireless transceiver adapted to receive electrical power from the wireless power receiver and to wirelessly send a signal that is based upon the measured characteristic; and
an air source mounted to the moveable chassis.

5. The apparatus of claim 4, wherein the air source comprises an air storage device and a coupling device adapted to receive air for storage in the air storage device.

6. An apparatus comprising:
a moveable chassis;
a wireless power receiver mounted to the moveable chassis and adapted to receive power wirelessly and convert the wireless power to electrical power;
a sensor mounted to the moveable chassis and adapted to receive electrical power from the wireless power receiver and to measure a characteristic of a continuous web material;
a wireless transceiver mounted to the moveable chassis, the wireless transceiver adapted to receive electrical power from the wireless power receiver and to wirelessly send a signal that is based upon the measured characteristic; and
a temperature control device mounted to the moveable chassis and adapted for at least one of heating and cooling the sensor.

7. A system comprising:
a wireless power source;
a track;
a chassis moveably coupled to the track and adapted to move back and forth across a surface of a continuous web material that is being manufactured or processed;
a wireless power receiver mounted to the chassis and adapted to inductively receive power wirelessly from the wireless power source and convert the wireless power to electrical power;
a sensor mounted to the chassis and adapted to receive electrical power from the wireless power receiver and to measure a characteristic of the continuous web material;
a wireless transceiver mounted to the chassis and adapted to receive electrical power from the wireless power receiver and to wirelessly send a first signal that is based upon the measured characteristic; and
a supervisory controller adapted to control motion of the chassis and to wirelessly receive the first signal.

8. The system of claim 7, further comprising:
a controller mounted to the chassis and adapted to receive a second signal based upon the measured characteristic and generate the first signal based upon the second signal.

9. The system of claim 7, further comprising:
a power storage device adapted to receive electrical power from the wireless power receiver and to provide electrical power to the sensor and the wireless transceiver.

10. The system of claim 7, further comprising:
a motor adapted to move the chassis.

11. The system of claim 7, wherein the wireless power source is adapted to move the chassis.

12. A system comprising:
a wireless power source;
a track;
a chassis moveably coupled to the track;
a wireless power receiver mounted to the chassis and adapted to receive power wirelessly from the wireless power source and convert the wireless power to electrical power;
a sensor mounted to the chassis and adapted to receive electrical power from the wireless power receiver and to measure a characteristic of a continuous web material;
a wireless transceiver mounted to the chassis and adapted to receive electrical power from the wireless power receiver and to wirelessly send a signal that is based upon the measured characteristic;
an air source mounted to the chassis; and
a supervisory controller adapted to control motion of the chassis and to wirelessly receive the signal.

13. The system of claim 12, further comprising:
an air supply device having a fitting;
wherein the air source comprises an air storage device and a coupling device adapted to couple to the fitting when the chassis is in a docking position and to receive air from the fitting for storage in the air storage device.

14. A system comprising:
a wireless power source;
a track;
a chassis moveably coupled to the track;
a wireless power receiver mounted to the chassis and adapted to receive power wirelessly from the wireless power source and convert the wireless power to electrical power;
a sensor mounted to the chassis and adapted to receive electrical power from the wireless power receiver and to measure a characteristic of a continuous web material;
a wireless transceiver mounted to the chassis and adapted to receive electrical power from the wireless power receiver and to wirelessly send a signal that is based upon the measured characteristic;
a temperature control device mounted to the moveable chassis and adapted for at least one of heating and cooling the sensor; and
a supervisory controller adapted to control motion of the chassis and to wirelessly receive the signal.

15. A method comprising:
inductively receiving power wirelessly from a wireless power source at a sensor, the sensor mounted to a chassis moveably coupled to a track and adapted to move back and forth across a surface of a continuous web material that is being manufactured or processed;
converting the wireless power to electrical power;
measuring a characteristic of the continuous web material using the sensor, the sensor operating with the electrical power; and
wirelessly transmitting a first signal that is based upon the measured characteristic using the electrical power.

16. The method of claim 15, further comprising:
storing the converted electrical power.

17. The method of claim 15, further comprising:
moving the sensor to a specified position relative to the continuous web material.

18. The method of claim 15, further comprising:
wirelessly receiving a second signal; and
configuring the sensor according to the second signal.

19. A method comprising:
receiving power wirelessly from a wireless power source at a sensor moveably coupled to a track;
converting the wireless power to electrical power;
in an air source, at least one of compressing air and storing compressed air;
measuring a characteristic of a continuous web material using the sensor, the sensor operating with the electrical power, wherein measuring the characteristic of the continuous web material comprises using air from the air source; and
wirelessly transmitting a signal that is based upon the measured characteristic using the electrical power.

20. A method comprising:
receiving power wirelessly from a wireless power source at a sensor moveably coupled to a track;
converting the wireless power to electrical power;
measuring a characteristic of a continuous web material using the sensor, the sensor operating with the electrical power;
wirelessly transmitting a signal that is based upon the measured characteristic using the electrical power; and
controlling a temperature of the sensor with a temperature control device, the temperature control device operating with the electrical power.

* * * * *